(12) United States Patent
Jørgensen

(10) Patent No.: US 8,141,418 B2
(45) Date of Patent: Mar. 27, 2012

(54) SAMPLING APPARATUS AND METHOD FOR SAMPLING

(75) Inventor: Thomas Kniep Jørgensen, Kolding (DK)

(73) Assignee: Source Technology ApS, Kolding (DK)

( * ) Notice: Subject to any disclaimer, the term of this patent is extended or adjusted under 35 U.S.C. 154(b) by 0 days.

(21) Appl. No.: 12/863,541

(22) PCT Filed: Jan. 21, 2009

(86) PCT No.: PCT/DK2009/000018
§ 371 (c)(1),
(2), (4) Date: Jul. 19, 2010

(87) PCT Pub. No.: WO2009/092378
PCT Pub. Date: Jul. 30, 2009

(65) Prior Publication Data
US 2010/0288040 A1      Nov. 18, 2010

(30) Foreign Application Priority Data
Jan. 21, 2008   (DK) .................................. 2008 00076

(51) Int. Cl.
*G01F 17/00*      (2006.01)
(52) U.S. Cl. .......................................................... 73/149
(58) Field of Classification Search ....................... 73/149
See application file for complete search history.

(56) References Cited

U.S. PATENT DOCUMENTS

| | | | | | |
|---|---|---|---|---|---|
| 3,156,120 | A | * | 11/1964 | Kowynia | 73/863.83 |
| 3,782,200 | A | * | 1/1974 | Maas | 73/863.51 |
| 5,563,384 | A | * | 10/1996 | Marlow et al. | 177/50 |
| 6,685,759 | B2 | * | 2/2004 | Dahlin et al. | 55/465 |

FOREIGN PATENT DOCUMENTS

| DE | 199 09 437 A1 | 9/2000 |
|---|---|---|
| DE | 19909437 A1 * | 9/2000 |

* cited by examiner

*Primary Examiner* — Lisa Caputo
*Assistant Examiner* — Jamel Williams
(74) *Attorney, Agent, or Firm* — Robert Mlotkowski Safran & Cole, P.C.; David S. Safran

(57) ABSTRACT

An apparatus and a method for sampling from a product flow, where the sampling is performed continuously and where the product is collected in a cup for determining physical conditions, for example, weight in relation to volume, and where the cup is emptied after ending the sampling. The apparatus is provided with at least one sampling cup provided with a filling opening and an emptying opening with different cross-sectional areas. It is not necessary to perform a turning movement of the sampling cup in order to empty it. Instead, preferably, the sampling cup is emptied by opening/uncovering the bottom. Emptying of the cup and subsequent cleaning of the cup are effected with open bottom by passage of the product flow through the cup; but, emptying may also occur in a separate duct.

9 Claims, 3 Drawing Sheets

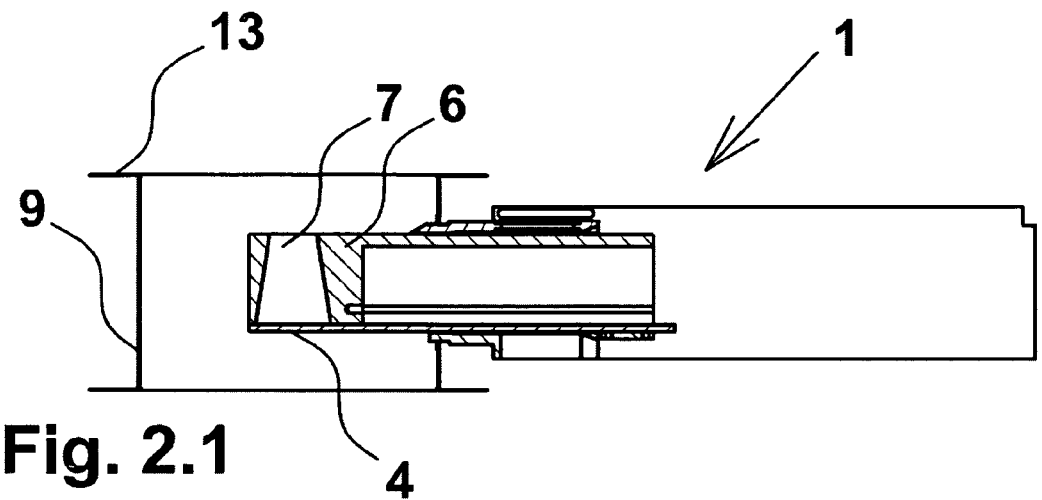
Fig. 2.1
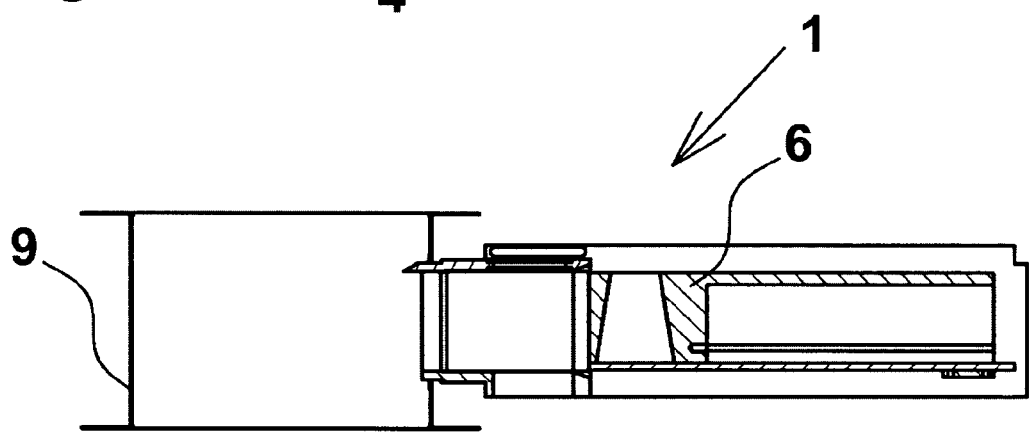
Fig. 2.2
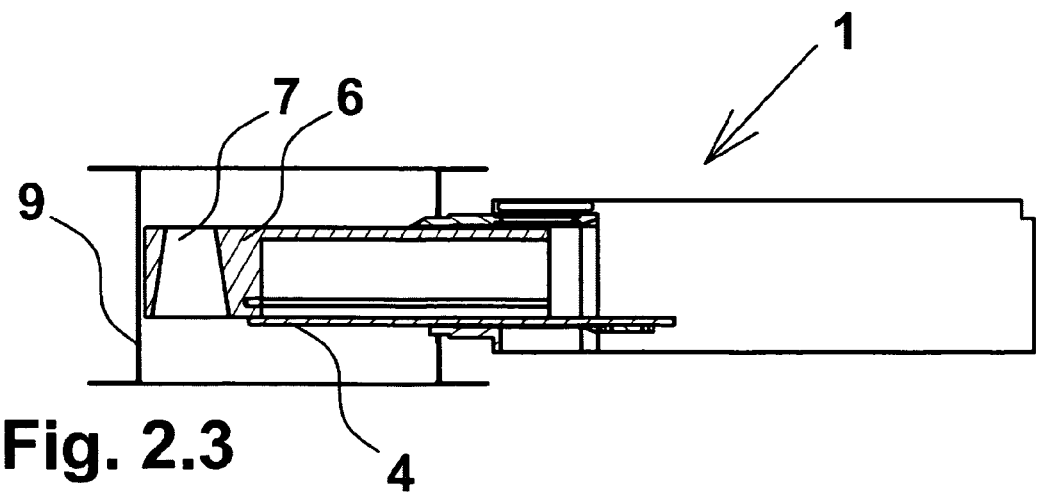
Fig. 2.3

SAMPLING APPARATUS AND METHOD FOR SAMPLING

BACKGROUND OF THE INVENTION

1. Field of the Invention

The present invention concerns an apparatus and a method for sampling from a product flow, where the sampling is performed continuously and where the product is collected in a cup, the cup being introduced directly into the product flow for subsequently determining weight in relation to volume or other physical conditions of the product, and wherein the cup is emptied after ending the sampling.

2. Description of Related Art

It is common knowledge to perform sampling, e.g., measuring density of products, such as, e.g., expanded and heat treated products, but also of other products where the products appear with a certain porosity during the manufacturing process, and where the product is desired to be continuously weighed in order thereby to regulate the processes controlling the expansion and thereby the porosity of the weighed product.

Density measurement is presently performed in various ways. Systems that are based on a specifically defined volume which is filled with products and weighed subsequently is the most widely used technique. This technique is frequently used at a purely manual level, where a process operator manually fills a tared container with a known volume with products. The container is often a traditional household measuring glass with closed bottom which is overfilled with product and subsequently leveled at the top such that the defined volume is completely filled with products. Subsequently, the container is weighed and the weight of the product in the defined volume may thereby be determined. This method of determining the density of a given product is used in production processes within many different industries, such as, e.g., processes for making food for animals, breakfast cereals, snacks, metal powder, fertilizer, wood and plastic.

During the making of these different products, which often occurs under high temperature by means of a compacting or extruding machine, the process parameters can be changed such that the texture of the given product is changed, entailing a change of the density of the product as well. A given product will frequently have a specific volume which is intended. This may, e.g., be in connection with filling of bags of a given product where a given density of a product is wanted in order thereby to optimally fill a package. By changing the addition of energy, moisture or similar process parameters for making a given product, the characteristic of the product can be changed and thereby also the density of the product. A process operator will therefore continuously check the density in order thereby to regulate the process if the density deviates from the specified value.

The problem of manual sampling or density measurement is that the repeatability is not great enough and that the weighing result therefore can only be used as an indication and not as a completely true value. This is due to the fact that a process operator is not able to fill a given sampling container in a uniform way. On this background, it has previously been attempted to construct automatic systems which may perform a continuous uniform sampling and weighing of the products. These systems are satisfactory for specific products and sizes of products; however, in industries as, e.g., those making snacks, breakfast products and feed for animals, the products are often relatively large and have a tendency to become sticky as a result of the heating process by which the product is formed.

The best known prior art for density weighing is based on a sampling cup with a closed bottom. The sampling cup is mounted on an arm which may be displaced horizontally and which is mounted on a weighing cell. The sampling cup is moved into a give product flow whereby the cup is (over)filled with product. When the cup is retracted to the weighing area, the sampling cup is scraped clean at the top in order to provide a defined volume of the product to be weighed. When the sample has been weighed, the cup is turned such that the product is emptied from the sampling cup. The prior art, however, has certain drawbacks that frequently cause the weight obtained to be as inaccurate as manual weighing, so that it can only be used as an approximate result. The drawbacks are the following:

1. The sampling cup with closed bottom. In density measurement of hot pellets, which is often the product, though not limited to such, the temperature of the product immediately before density measurement will often be about the boiling point of water as a result of the heating process. The density in the manufacturing process is flexible and easily influenced. By collecting a given sample for measurement, a condensation of vapor will start during collecting in the cup. The product as well as dust and crumbs will stick to the cup upon emptying. After some time, deposits will appear in the sampling cup which will cause the presumed volume in the sampling cup used for collecting the product to be reduced, and the weighing result thereby will no longer be accurate.

Attempts to clean the sampling cup, either with compressed air or rotating brushes, have not appeared to be sufficiently effective.

2. Scraping the sampling cup is an essential part of the system. The more homogenous scraping of the sampling cup is, the more precise weighing. As the prior art uses a cup with a closed bottom, it requires a large diameter in order to achieve a reasonable volume for the product, at the same time generating a large scraping area and thereby leading to fluctuating measuring results. In general, the best weighing result is achieved by the largest possible volume and the smallest scraping area in the sampling cup. Since the products are often hot and sticky, scraping of the sampling cup can imply that large lumps are entrained, causing large deviations in the weighing result.

3. Hygiene is essential in manufacturing processes for products forming part of the food chain. Since cleaning cannot be done efficiently by the prior art, either by the product flow or in other mechanical ways, a hygiene problem arises whereby bacteria cultures as e.g., salmonella can appear.

4. The installation height of a given density measuring apparatus is very critical as many processing plants have very little spacing between two processing machines available. The prior art is very space consuming due to the technical embodiment, where compensation is made for the design of the sampling cup with closed bottom by increasing the diameter and the height, respectively, and large changes in the processing plant are therefore required, if possible at all.

An apparatus is known from DE 199 09 437 for taking a sample in a product flow where the sample is taken by a sampling cup with an upper and a lower plate that close and open the filling and emptying openings, respectively. This sampling cup is cleaned by compressed air which partly may provide for the cleaning of the sampling cup. However, there is the disadvantage that possible accumulation of residues of a sticky product cannot entirely be avoided, entailing that it is required with a regular manual cleaning of the sampling cup.

SUMMARY OF THE INVENTION

It is thus the purpose of the invention to provide a solution that is secure, precise and takes into account the above mentioned disadvantages.

As mentioned in the introduction, the invention concerns an apparatus and a method for sampling from a product flow, where the sampling is performed continuously and where the product is collected in a cup, said cup being introduced directly into the product flow for subsequently determining weight in relation to volume or other physical conditions of the product, and where the cup is emptied after ending the sampling.

The apparatus according to the invention is provided with at least one sampling cup, where the cup is provided with a filling opening with a cross-sectional area and with an emptying opening with a different cross-sectional area, respectively.

It is thus a sampling cup where the product is not emptied by the same opening through which it is filled. Therefore, an apparatus according to the invention may be designed in a simple and reliable way as it is not necessary to perform a turning movement of the sampling cup in order to empty it.

A further embodiment of an apparatus for sampling according to the invention is, in a preferred form, provided with a filling opening of the cup that has a cross-sectional area which is less than the cross-sectional area of the emptying opening. Thus, a cup with a given volume with relatively small surface area is achieved. The small or minimal surface area causes the leveling taking place when the cup is drawn out of the product flow to become much more exact than if there were a larger surface area. At the same time, the desired volume is maintained whereby a great and sufficient measuring accuracy can be achieved.

A method for sampling according to the invention includes at least steps where a sampling cup is introduced into a product flow whereby the cup is filled, wherein the sampling cup is withdrawn, scraped level and weighed, wherein the sampling cup is emptied by uncovering the bottom, and subsequently, cleaned with the bottom open, after which the bottom is covered and the system is ready for the next weighing. Emptying of the cup is preferably effected in the product flow, but may also occur in a separate duct intended for that purpose.

In a preferred embodiment of an apparatus according to the invention, the apparatus includes at least one cup, where the cup is provided with a sliding bottom. By using a sliding bottom, the weighed product may easily be emptied in the product flow, and by a sliding bottom is achieved a particularly advantageous solution where possible deposits of the product on the bottom are scraped off by sliding the bottom.

In one variant of the invention, the apparatus may be provided with a compressed air device for cleaning the interior of the cup. Possible residues in the form of dust or crumbs of the product may thus be removed from the sampling cup.

The method for sampling from a product flow according to the invention may advantageously be provided with a step wherein the sampling cup is cleaned by compressed air, but is preferably provided with a step wherein cleaning is effected by means of the product flowing through the open cup. The cleaning is thus effected by products scraping against the surface in the cup with the bottom open.

It is a characteristic of all heat treatment processes that control of density is essential for the physical as well as nutritional quality of the product. The problem of achieving a uniform continuous density measurement by the ability of the prior art technologies that have sufficient flexibility for handling many different product characteristics and providing such great repeatability that the value can be used for documentation is commonly known.

In order to solve this problem, by the new invention, it has been found that there may be provided an accurate and continuous measurement of the density of the product by means of several independent process technical solutions. It has been found that, by making a bottomless sampling cup, it may be avoided that products and dust particles accumulate at the bottom of the sampling cup. By having a bottomless sampling cup, the product flow may thereby be used as cleaning medium for the cup during emptying. By supporting the bottomless sampling cup during emptying, one may still measure a product weight in a controlled volume without risk of accumulating foreign bodies that reduce the weighing result. Also, it has been found that by making a bottomless sampling cup, the design of the cup can be made such that a minimal scraping area occurs. By, e.g., making a smaller diameter at the top than at the bottom, a very small scraping area is attained, considerably improving the weighing accuracy and the repeatability.

By means of the present invention, such an exact weighing result may be achieved that it is immediately usable for regulating the process parameters used in the process for making the weighed products, e.g., for regulating a heat treatment process. The producer of a given product may thereby ensure that the declaration of contents is followed exactly with regard to density. Also, the hygiene of the process for density measurement will be substantially improved because the system is self-cleaning, since the product flow will prevent local areas at which the product can accumulate and bacteria cultures be formed. Due to the bottomless sampling cup, a large volume is attained at a small height, simultaneously improving the possibilities for installing the system between the product processes.

An apparatus and a method for sampling in a product flow may furthermore include determination of the density of a "compacted" product, after which the compaction index of the product can be determined. Determining the compacted density of a product is traditionally determined by taking a product sample manually in a measuring glass with a given volume. The density may then be determined by manual weighing, or the density is alternatively determined via a sampling cup with a well-defined volume which is introduced in the product flow and weighed afterwards. The sample is then vibrated, and the product compacted or "compacted" hereby, and finally the density of the compacted product may be determined by manual reading of the compacted volume which now may be put in relation to the weight of the sample. This process is manual and resource-demanding and may advantageously be substituted by a new automatic process.

This new process is, in principle, independent of the design of the automatic sampling equipment itself and therefore not limited to sampling cups with, e.g., conical sides, but may be used for all thinkable embodiments of sampling cups, when only these can take out a sample with a constant and well-defined volume.

This may be done with an apparatus according to the invention where a sample is taken with an apparatus as mentioned above and which furthermore is equipped with means for compacting or compacting of the contents in the filled sampling cup. These means may, e.g., impart a mechanical action on the sampling cup and possibly constituted by a known type of vibrator/oscillator which is mounted in connection with the sampling cup. After ending the compacting, the volume of the sample can be determined by camera reading of, e.g., a scale on the sampling cup. Alternatively, the volume can be determined via telemeter which is used for determining how far the product has sunk into the sampling cup.

By knowing these data, the density of the product as well as the compacted density may be determined rapidly without using staff to perform a protracted manual measurement.

Compacting may, as mentioned, advantageously be effected by providing the apparatus according to the invention with a vibrator/oscillator of suitable type. The vibrator may advantageously be arranged such that at least the sampling cup is vibrated. This vibration may in principle be initiated at the same moment as the sampling cup is withdrawn from the product flow or when a lid is put on the filling opening in the sampling cup.

The frequency by which "compacting" is performed may be adapted individually to various products, and similarly the time of "compacting" may be regulated such that a desired result is achieved.

A further advantage of an apparatus according to the invention which may perform a density determination of a "loose" product sample as well as of a "compacted" (compressed) product sample is that the results of the performed measurements may immediately be used as regulating parameters for the preceding process or processes as well as for one or more succeeding processes. A much better and not the least more rapid regulation of respective parameters may hereby be achieved in that regulation can be performed immediately after ending density determination, without having to do a manual process before regulation. Moreover, there is the obvious advantage that regulation can be performed much more often, as in principle density determination can be performed continually—one after another—and the results may instantaneously be introduced to a continuous regulation. By such a continuous regulation is achieved a much better result while at the same time the risk of regulation errors is greatly minimized since there is no need for human data processing before a regulating action. The measured values for the densities may, e.g., be expressed as analogous signals of 4-20 mA which immediately can be used as input in various process regulating systems.

A further advantage of measuring the "compacted" density in connection with a sampling cup is that simultaneously a water measurement of the sample can be performed. Such a measurement is typically performed with microwave equipment and the measuring accuracy is much more exact in a compacted sample than in a loose sample. Also, the more exact measurement of the water content in a sample may be used for regulating preceding and/or subsequent processes. Again, the great advantage that rapid regulation can be effected is achieved, and thereby greater certainty that the process is running as expected and that the quality of the product maintains the desired quality. Processes where the measured data can be used for regulation may, e.g., be drying and/or cooling, but other processes may be controlled and regulated as well on the background of the measured densities and the water content of the product.

Embodiments of the invention are described in detail in the following with reference to the accompanying drawings.

BRIEF DESCRIPTION OF THE DRAWINGS

FIGS. 2.1-2.3 show the apparatus in various positions.

DETAILED DESCRIPTION OF THE INVENTION

As previously mentioned, the invention concerns a system which can be mounted at any place in a manufacturing process for diverse products where, e.g., a density determination may be of interest. The density measurement according to the invention is developed with regard to a more optimal design which will facilitate cleaning of the sampling cup and while, at the same time, the scraping off of the product may be substantially reduced in order thereby to improve the weighing result. Furthermore, other measurements may be performed in the sample taken by the sampling cup, whereby a plurality of physical conditions of the product may be determined and used as regulating parameter.

Figure 1:
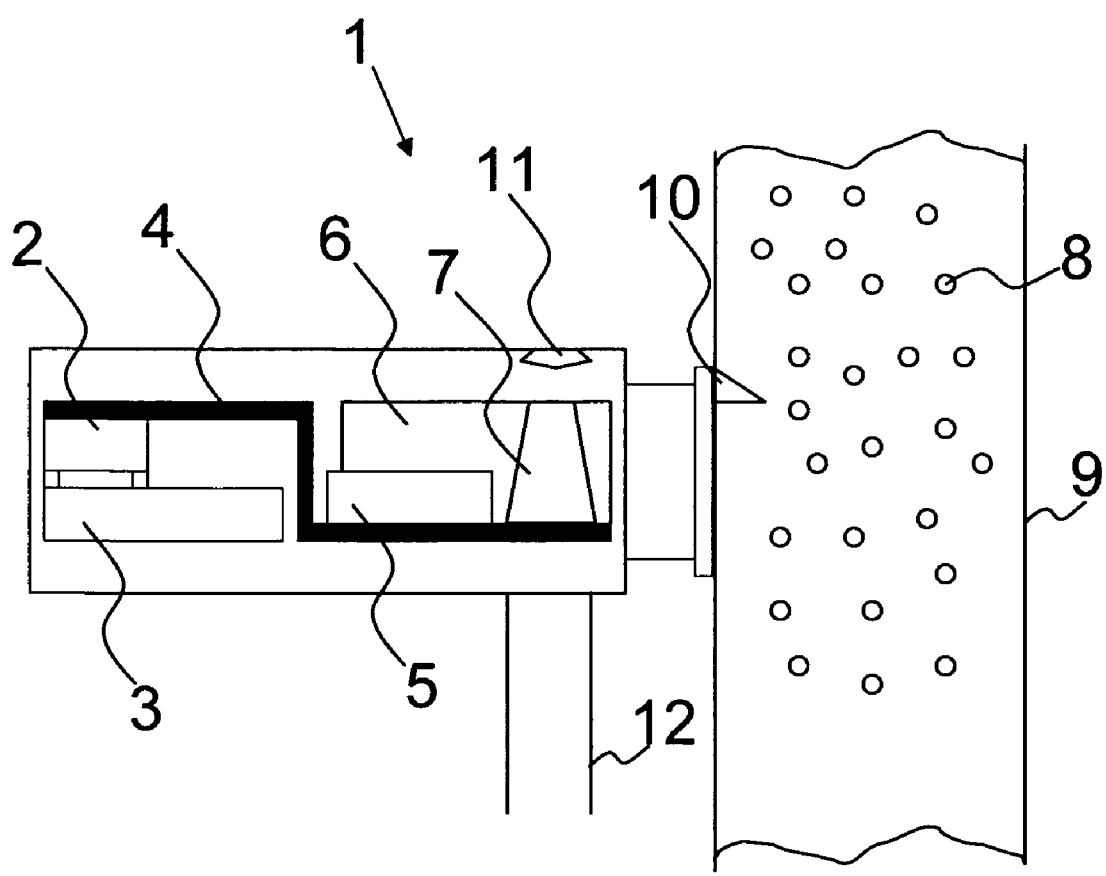
FIG. 1 is a sectional side view of a sampling apparatus mounted on a channel section with a product flow.

In FIG. 1 is seen the system 1 which comprises a weighing cell 2 mounted on a first actuator 3 which is displaceable back and forth in horizontal direction. On the weighing cell 2, an arm 4 on which is mounted a further actuator 5. A sampling cup 6 is mounted in connection with the actuator 5 in the form of a piston, The a sampling cup 6 is provided with a hole 7 for filling with product 8.

In FIG. 1, the system 1 also is shown mounted on a channel section 9 into which a flow of product falls. By horizontal displacement of the first actuator 3, the sampling cup 6 is moved into the product flow 8 whereby the product 8 fills the cup 6. The sampling cup 6 is made without a bottom and is of hollow cylindric, conical or other geometric shape with a bottomless hole 7. The sampling cup 6 is supported by the arm 1 in a manner such that the arm acts as bottom for the sampling cup 6 as the cup 6 is filled the product 8 so that the product 8 does not fall out of the bottom. After the cup has been within the product flow 8 for a given period of time, the first actuator 3 is horizontally displaced to its initial position, and excess material filled in the cup 6 is scraped off by scraper 10. Immediately after withdrawal of the sampling cup 6, a weighing via the weighing cell 2 is performed. When the actual weighing result is defined, the sampling cup 6 is displaced horizontally again by means of the first actuator 3. When the sampling cup 6 is placed again in the product flow 8, the second actuator 5 is activated such that the sampling cup 6 is displaced again in relation to the arm 4. The bottom of the sampling cup 6 is thereby opened/uncovered and the weighed product 8 flows out.

The product flow 8 falling by the force of gravity will simultaneously clean the cup 6 from above. This is only effected in that the surface in the hole 7 is touched by the product flow 8. After a given period of time, the sampling cup is again horizontally displaced via the first actuator 3 while the second actuator 5 is still in the extended position. The sampling cup 6 is thus still horizontally displaced from the arm 4 and therefore with its bottom open enabling free passage through the hole 7. After a given period of time, a compressed air nozzle 11 is activated, whereby compressed air blows possible particles out of the sampling cup 6. Possible dust particles are discharged through discharge pipe 12 under the system 1. After a given period of time, the second actuator 5 is horizontally displaced whereby the sampling cup 6 is again supported by the arm 4. Before a new sampling is performed, the weighing result is reset.

FIGS. 2.1-2.3 show a sequence in which the sampling apparatus 1 is seen in three different positions. The apparatus is shown schematically while various elements, such as, e.g., the actuators 3, 5, are not shown.

In FIG. 2.1, the sampling cup 6 is shown in an extended position within the channel 9, which is here shown as a channel section with flanges 13 for bolt mounting in a channel, where the hole 7 is made with a conical geometry and with an upward facing opening by which it is filled with the product 8 flowing in the channel 9.

In FIG. 2.2, the sampling cup 6 is withdrawn into the apparatus 1 for determining physical conditions of the product, e.g., determining weight by means of a weighing cell 2 (not shown) in relation to the specific volume in the sampling cup 6. Other conditions of the product 8, e.g., water content, may also be determined in the apparatus 1, e.g., by photocells, microwave technique or other methods.

Finally, FIG. 2.3 shows the sampling cup 6 displaced into the channel 9 and the sampling cup 6 with the hole 7 displaced in relation to the arm 4 that otherwise forms the bottom in the sampling cup 6. In this position, emptying of the product 8 which has just been examined occurs, and subsequently, passage through the hole 7 of the flowing products 8 in the channel 9 occurs. As a result, the side of the hole 7 is cleaned from possible deposits of the just emptied product 8. This cleaning process may in principle be compared with a "shot blasting" of an item, where the "shot" is here constituted by the product flow 8.

Figure 3:
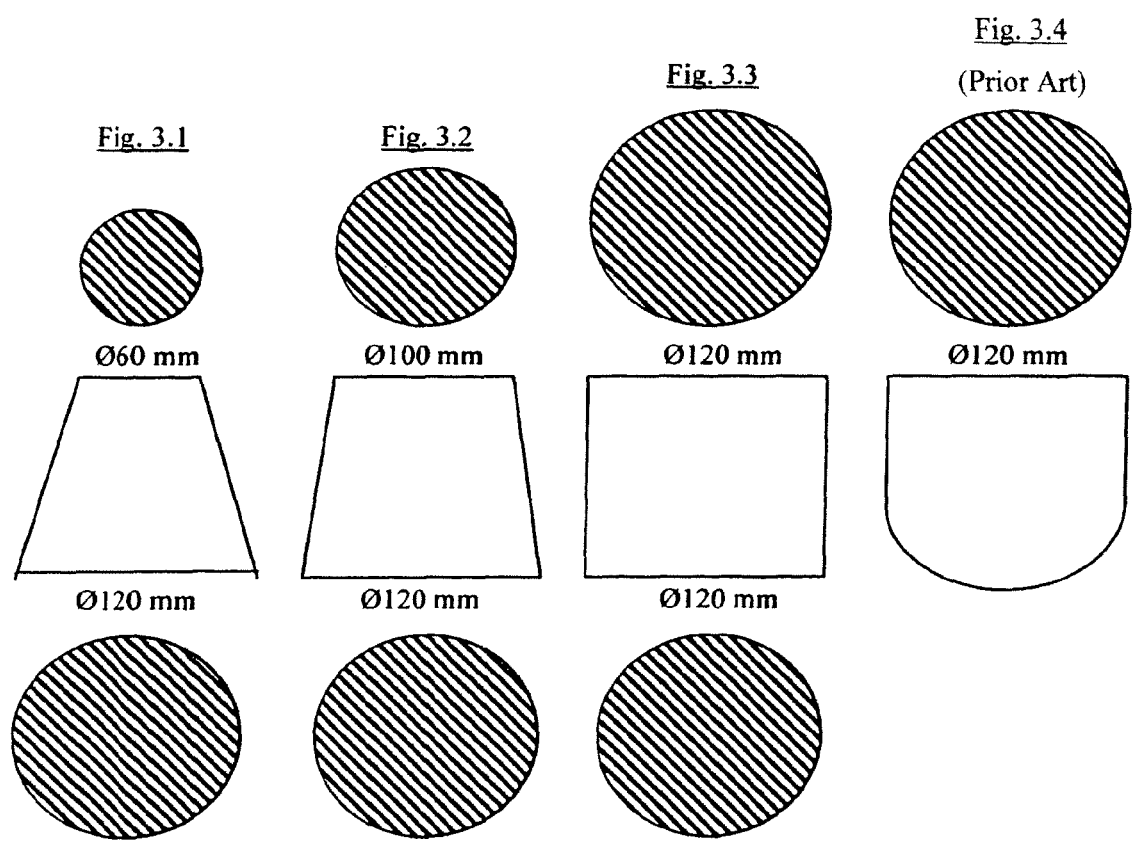
FIGS. 3.1-3.4 show examples of different designs of sampling cups.

In a controlled experiment on a process line for making dog feed, it has been found that the design of the cup with regard to the scraping area has a great influence on the weighing result. In FIG. 3 are shown four different cup designs which have been tested in production of dog feed:

FIG. 3.1 shows a conical design with top diameter (ø) of 60 mm top and a ø of 120 mm at the bottom.

FIG. 3.2 shows a conical design with top ø of 100 mm top and a bottom ø of 120 mm.

FIG. 3.3 shows a cylindrical hole with ø120 mm top and ø120 mm bottom

FIG. 3.4 shows a prior art configuration with a closed bottom.

Data for Experiment
Type of feed: Extruded dog feed
Diameter of feed: ø18.2 mm
Thickness of feed: 10.4 mm
Specified density: 385 g/l
Humidity: 26% water
Temperature of feed: 80-85° C.

The volumes of the various cups used in the experiment were identical as shown on the table below:

| Cup design | Dimension | Volume of cup | Scraping area | Drawing |
| --- | --- | --- | --- | --- |
| Cone | ø60-ø120 mm | 1000 ml | 2.826 mm² | FIG. 3.1 |
| Cone | ø100-ø120 mm | 1000 ml | 7.850 mm² | FIG. 3.2 |
| Cylindric | ø120-ø120 mm | 1000 ml | 11.304 mm² | FIG. 3.3 |
| Closed cup | ø120 mm | 1000 ml | 11.304 mm² | FIG. 3.4 |

EXPERIMENT

By controlled experiments it could be demonstrated that by having a reduced scraping area, very accurate weighing results can be produced as compared with prior art.

| Measurement no.: | FIG. 3.1 | FIG. 3.2 | FIG. 3.3 | FIG. 3.4 |
| --- | --- | --- | --- | --- |
| 1 | 382 | 380 | 378 | 371 |
| 2 | 381 | 380 | 376 | 382 |
| 3 | 383 | 378 | 384 | 397 |
| 4 | 384 | 384 | 386 | 385 |
| 5 | 380 | 385 | 389 | 374 |
| 6 | 385 | 386 | 379 | 391 |
| 7 | 381 | 380 | 385 | 381 |
| 8 | 379 | 382 | 393 | 370 |
| 9 | 382 | 377 | 384 | 373 |
| 10 | 384 | 376 | 388 | 400 |
| 11 | 382 | 379 | 379 | 389 |
| 12 | 379 | 378 | 386 | 377 |
| 13 | 382 | 381 | 377 | 398 |
| 14 | 383 | 383 | 381 | 373 |
| 15 | 384 | 386 | 377 | 379 |
| 16 | 382 | 384 | 391 | 395 |
| 17 | 382 | 383 | 384 | 378 |
| 18 | 379 | 379 | 391 | 389 |
| 19 | 384 | 376 | 393 | 397 |
| 20 | 385 | 386 | 381 | 378 |
| Max. deviation | ±3 g/l | ±5 g/l | ±8 g/l | ±15 g/l |

It appears from the above table that the smallest deviations are achieved by the three variants using a sampling cup with opening bottom. Moreover, a clearly smaller deviation appears by the two sampling cups that have a conical shape and with smaller filling opening that discharge opening. The deviation is particularly small by the sampling cup shown in FIG. 3.1.

The invention claimed is:

1. Sampling apparatus for continuous sampling from a product flow, comprising:
   at least one sampling cup positioned for being introduced directly into the product flow, having a filling opening at the top for receiving a sample and an emptying opening for emptying the cup, wherein the cross-sectional area of the filling opening is less than the cross-sectional area of the emptying opening, and
   means for moving the at least one sampling cup into and out of the product flow.

2. Sampling apparatus according to claim 1, wherein a closure is provided slidingly covering and uncovering the emptying opening of the at least one sampling cup.

3. Sampling apparatus according to claim 1, further comprising a compressed air device for cleaning the interior of the sampling cup.

4. Sampling apparatus according to claim 1, further comprising vibrating means for compacting the removed sample.

5. Sampling apparatus according to claim 4, wherein the apparatus includes reading means for determining product volume in the sampling cup after compacting the sample, where the reading means preferably is constituted by a camera or a telemeter.

6. Sampling apparatus according to claim 5, wherein the reading means is directly or indirectly connected with one or more control units in connection with preceding or succeeding processes in the production facility in which the apparatus is arranged.

7. A method for sampling from a continuous product flow, comprising at least the following steps:
   introducing a sampling cup, having a filling opening the cross-sectional area of which is less than the cross-sectional area of an emptying opening of the sampling cup, into a product flow to obtain a sample by filing the cup with product from the product flow;
   withdrawing the sampling cup from the product flow, scraping the top of the sampling cup to level product filled therein and obtaining the weight of the product contained in the sampling cup;

emptying the sampling cup by opening a bottom end of the sampling cup;

cleaning the sampling cup with the bottom end of the sampling cup open by directing a cleaning flow through the filling and emptying openings;

closing the bottom end of the sampling cup in preparation for obtaining another sample.

8. Method for sampling from a product flow according to claim 7, comprising the further step of cleaning the sampling cup with compressed air.

9. Method for sampling from a product flow according to claim 7, the step of cleaning the sampling cup using the product flowing through the open cup as said cleaning flow.

* * * * *